United States Patent [19]

Michaelis et al.

[11] Patent Number: 4,539,649

[45] Date of Patent: Sep. 3, 1985

[54] METHOD AND APPARATUS FOR THE GAMMA TRANSMISSION ANALYSIS OF MULTICOMPONENT MIXTURES IN THE PRESENCE OF COARSE GRAINED COMPONENTS

[75] Inventors: Walfried Michaelis, Seevetal; Hans-Ulrich Fanger, Reinbek; Hans L. The, Hamburg, all of Fed. Rep. of Germany

[73] Assignee: GKSS-Forschungszentrum Geesthacht GmbH, Geesthacht, Fed. Rep. of Germany

[21] Appl. No.: 417,896

[22] Filed: Sep. 14, 1982

[30] Foreign Application Priority Data

Sep. 25, 1981 [DE] Fed. Rep. of Germany ....... 3138159

[51] Int. Cl.³ .......................... G06F 15/46; G01F 1/00
[52] U.S. Cl. ..................... 364/558; 364/510; 378/53
[58] Field of Search ............... 364/558, 564, 509, 510, 364/527; 378/51, 53, 54, 57

[56] References Cited

U.S. PATENT DOCUMENTS

| | | | |
|---|---|---|---|
| 3,265,873 | 8/1966 | Sawyer | 364/510 X |
| 3,776,034 | 12/1973 | Kolb | 364/510 X |
| 4,001,589 | 1/1977 | Arima et al. | 378/53 X |
| 4,096,028 | 1/1978 | Rosenberger | 364/510 X |
| 4,205,230 | 5/1980 | Stubbs | 378/51 X |
| 4,414,472 | 11/1983 | Watt | 378/53 X |
| 4,419,898 | 12/1983 | Zanker et al. | 364/510 X |

Primary Examiner—Edward J. Wise
Attorney, Agent, or Firm—Spencer & Frank

[57] ABSTRACT

Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating the relation between the transmitted and detected radiation to determine the average density or volume percentage by using a transmission equation applicable to homogeneous mixtures, the evaluation including transforming the values resulting from solving such equation, or a selected term of such equation, with the aid of a correction function which is derived by comparison of corresponding values in the transmission equation applicable to the homogeneous mixtures and in a further transmission equation which is dependent on the particle sizes of the coarse grained component in order to provide a corrected determination relative to that component.

17 Claims, 13 Drawing Figures

METHOD AND APPARATUS FOR THE GAMMA TRANSMISSION ANALYSIS OF MULTICOMPONENT MIXTURES IN THE PRESENCE OF COARSE GRAINED COMPONENTS

BACKGROUND OF THE INVENTION

The present invention relates to a method and apparatus for determining the average density or volume percentage of a multicomponent mixture by means of gamma transmission analysis.

Flow engineered transport through pipelines is a very advantageous conveying method, not only for gases or liquids, but also for solids. Because of many advantages, such as simplicity, environmental safety, independence of weather, ease of maintenance and the like, the hydraulic transport of solids has become very widespread in the past decades and is gaining in significance today. Most important is the hydraulic transport of raw materials over long distances, as, for example, the transport of ores and coal over long overland routes or, in the future, the transport of marine raw material deposits (manganese modules, ore slurries and the like) mined in the deep sea.

Compared to all competing conveying systems, hydraulic transportation of solids has interesting economic prospects for large conveying quantities and distances with respect to the specific transportation costs. Prerequisite for reliability and economy of such conveying systems is the control and optimization of the transport parameters.

German Auslegeschrift [Published Patent Application] No. 2,622,175 discloses a method which permits, without contacting the material being transported, determination of the most important conveying stream parameters such as, for example, parts by volume of individual components or average density.

This method is based essentially on the fact that for two substances, p and q, having a sufficiently different atomic number z, the ratio of their gamma absorption coefficients, i.e. $\mu_p/\mu_q$, in the region of low gamma energies up to about 1.5 MeV exhibits a distinct energy dependence.

In this way it is possible to unequivocally determine the two unknown component shares or volume percentages $v_p$ and $v_q$ of these components by way of a measurement of the transmitted intensities J with and without absorbing body at two different gamma energies, $E_1$ and $E_2$, produced by gamma sources, represented in two equations. The "volume percentage" is the percentage, by volume, of the corresponding component in the total mixture.

Since generally the measuring geometry is fixed and thus the length L of the transmission path in the irradiated medium is constant, the third component results as an ancillary product from the marginal condition that the sum of the three volume percentages must be 100%. When this method is used in the hydraulic conveying art, the third component is water (w) or another liquid which generally takes up the space in the conveying pipe left by the solid components p and q. In this case it is advisable not to select, as the reference parameter, the absorber free, or vacuum, intensity but the intensity $J_w$ of the gamma radiation for water, or some other conveying medium, without solids. The two transmission equations for energies $E_1$ and $E_2$ are then as follows:

For energy $E_1$:

$$t_1 = \frac{J_1}{J_{w1}} e^{-L[v_p\mu_{p1} + v_q\mu_{q1} - (v_p + v_q)\mu_{w1}]} \quad (1)$$

For energy $E_2$:

$$t_2 = \frac{J_2}{J_{w2}} e^{-L[v_p\mu_{p2} + v_q\mu_{q2} - (v_p + v_q)\mu_{w2}]} \quad (2)$$

where $$v_p + v_q + v_w = 1. \quad (3)$$

and $\mu$ are the corresponding gamma absorption coefficients.

Solving these equations for $v_p$ and $v_q$ results in $$v_p = (LN)^{-1}[-\ln t_1(\mu_{q2} - \mu_{w2}) + \ln t_2(\mu_{q1} - \mu_{w1})] \quad (4)$$

and, $$v_q = (LN)^{-1}[\ln t_1(\mu_{p2}) - \ln t_2(\mu_{p1} - \mu_{w1})] \quad (5)$$

where $$N = (\mu_{p1} - \mu_{w1})(\mu_{q2} - \mu_{w2}) - (\mu_{p2} - \mu_{w2})(\mu_{q1} - \mu_{w1}). \quad (6)$$

The gamma radiation at two energies can here pass in an advantageous manner through the measuring volume on a common beam axis and thus cover exactly the same volume portions. Different physical structures, which would lead to inhomogeneity errors in transmission of the two energies at different locations, thus produce no effect.

Of course this method can also be used for more than three components. An additional gamma energy is then required for each additional component. One further transmission equation then results in the calculation for each additional component.

Other, less precise, methods of gamma absorptiometry employ only one gamma energy to monitor the conveying stream, preferably with the use of the simple Lambert-Beer theorem, or they do not irradiate the measuring volume on a common beam axis but on separate beam axes, as described by J. S. Watt and W. J. Howarth, in IAEA Report Helsinki, 1972, IAEA/SM-159/1.

All known methods have in common that homogeneity of the multicomponent mixture within the measuring volume is implicitly assumed to exist, i.e. the influence of the particle sizes is assumed to be negligible. However in those cases where the particle sizes are finite, e.g. raw coal, gravel or manganese modules, the analysis may furnish results that differ from reality since, due to the nonlinearity of the law of the attenuation of gamma radiation, the data determined from the transmission equations are systematically falsified.

The nature of this particle size problem will be clarified with the aid of FIGS. 1a and 1b. For the sake of simplicity, there is assumed to be a two-component mixture consisting of the substances, or components, A and B. Component A completely absorbs the gamma radiation and component B is completely transmissive thereof. In the case of essentially homogeneous mixture depicted on the left side of FIG. 1a, complete absorption occurs because no gamma quanta are passed through component A, which is illustrated correctly by the so-called "sandwich model" at the right side of FIG. 1a. In contradistinction thereto, in the case of an inhomogeneous mixture, as depicted on the left side of FIG. 1b, there always exists a finite probability that only part of the gamma radiation is absorbed, in contrast to the complete absorption in the first case. The illustration in the form of the sandwich model then furnishes the wrong image.

From this conceptual model it can be seen that in spite of the same volume concentrations in both mixtures, different residual intensities are measured in the cases of the homogeneous mixture and the inhomogeneous mixture. The inhomogeneity therefore furnishes—seen locally—greatly differing absorption for the gamma rays, depending on the presence and spatial distribution as well as size of the coarse grained particles. Therefore the sandwich model which applies only for homogeneous mixtures cannot always be used.

SUMMARY OF THE INVENTION

It is therefore an object of the present invention to improve the method and apparatus of the above-mentioned type in such a way that particle size influence is also detected and correct results are obtained in spite of finite particle sizes.

The above and other objects are achieved, according to the invention, by a method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating the relation between the transmitted and detected radiation to determine the average density or volume percentage by using a transmission equation applicable to homogeneous mixtures, the step of evaluating including transforming the values resulting from solving such equation, or a selected term of such equation, with the aid of a correction function which is derived by comparison of corresponding values in the transmission equation applicable to the homogeneous mixtures with a further transmission equation which is dependent on measured particle sizes of the coarse grained component in order to provide a corrected determination relative to that component.

DESCRIPTION OF THE PREFERRED EMBODIMENTS

Figure 1A:
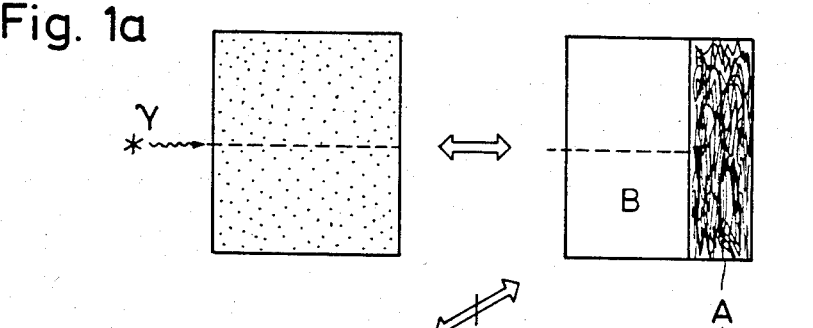
FIGS. 1a and 1b are pictorial models of two component mixtures and have already been described in detail.
Figure 1B:
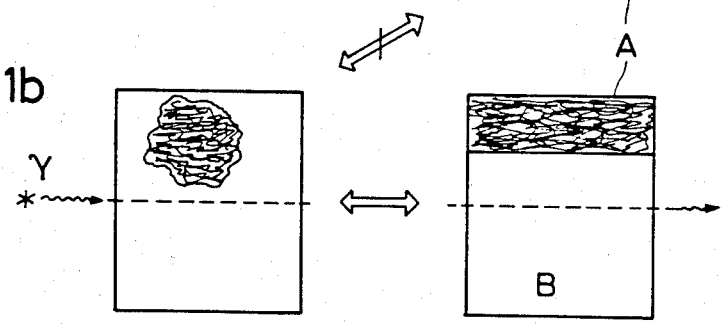
Figure 2A:
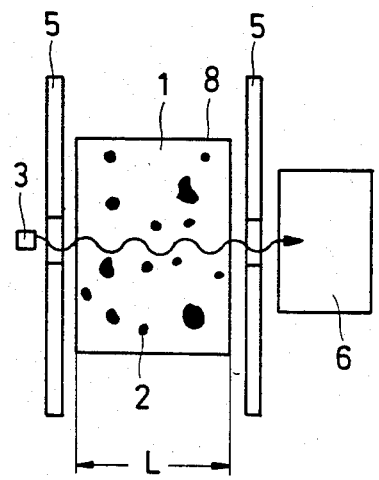
FIGS. 2a-2d are simplified pictorial cross-sectional, end views of pipeline systems equipped with embodiments of monitoring systems for carrying out the invention.
Figure 2B:
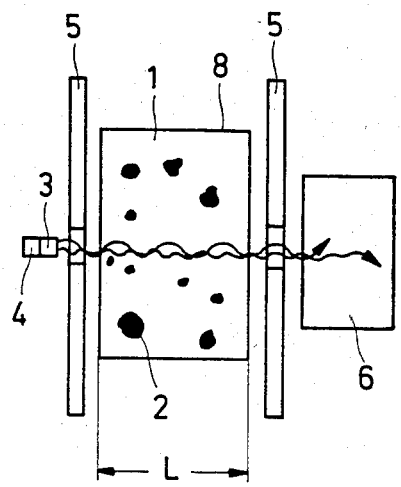
Figure 2C:
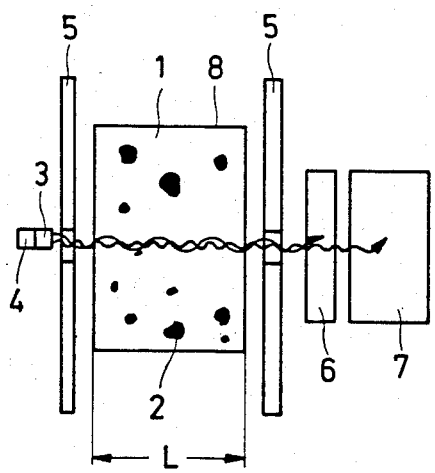
Figure 2D:
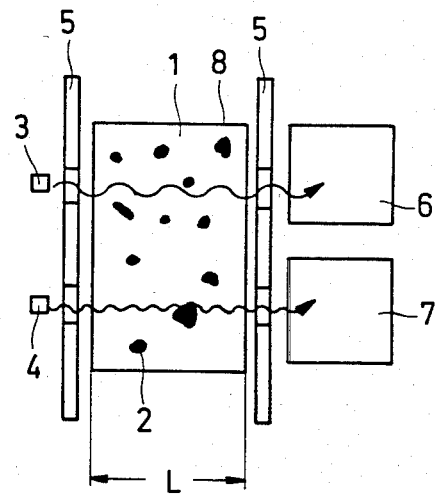

According to the invention and as shown in FIGS. 2a-2d, a multicomponent mixture 1, which contains one or more coarse-grained components 2 and is being conveyed through a conduit 8 is irradiated with radiation from one or simultaneously in succession from a plurality of gamma radiation sources 3, 4 producing different energies possibly with the aid of suitable collimators 5, and the transmitted radiation is detected by means of one or a plurality of series or parallel arranged detectors 6, 7. In FIG. 2a there are one source 3 and one detector 6. This arrangement is used only for measuring the average density. In FIG. 2b there are two sources 3 and 4 transmitting along a single axis and one detector 6. In FIGS. 2c and 2d there are two sources 3 and 4, and two detectors 6 and 7, a common beam axis being established in FIG. 2c and parallel, vertically spaced axes existing in FIG. 2d.

Since generally the measuring geometry is fixed, the length L of the transmission path in the irradiated medium is constant and known. By solving transmission equations in the form of equations (1) and (2), the measured transmissions are evaluated with respect to the volume percentage or average mixture densities.

In order to consider the particle size influence, however, the invention provides that the measured transmission values t or the products of volume percentage v and absorption coefficient $\mu$ of the coarse grained components 2, reduced by the absorption coefficient of the rest of the mixture $\mu_g$; or the volume percentages $v_p$ of the coarse grained components 2 or the absorption coefficients $\mu_p$ of the coarse grained component 2, reduced by the absorption coefficient $\mu_g$ of the rest of the mixture; or the absorption coefficients $\mu_p$ of the coarse grained components 2, are transformed with the aid of correction functions. The radii r of the particles are either known or, as will be described below, are determined with the same or a parallel measuring device.

According to the invention, the correction functions are derived, from a transmission equation which depends on the particle size, by a comparison of the coefficients with the transmission equations applicable for homogeneous mixtures.

FIG. 2a is a schematic representation of a measuring device having only one gamma source 3 and only one detector 6. According to the above-described process, this device is suitable for the approximate determination of the average mixture density of a mixture with coarse grained components.

In FIG. 2b, two sources 3 and 4 are employed and the gamma radiation on the common beam axis is detected with only one detector 6. The radiation is subject to spectroscopic analysis to separate the two transmission energy values. This apparatus permits the determination of the parts by volume of a three component mixture having coarse grained components and permits a more precise determination of the average mixture density than the arrangement of FIG. 2a.

The same performance as the apparatus of FIG. 2b is provided by a measuring device of the type shown in FIG. 2c. Here, two detectors 6 and 7 are employed, each being substantially sensitive to only one of the gamma energies employed (e.g. 60 keV and 662 keV). The apparatus shown in FIGS. 2b and 2c employ two sources 3 and 4 which emit along a common beam axis.

FIG. 2d shows a measuring arrangement with separate beam axes.

According to the invention, the particle size dependent transmission equation for the radiation attenuation as a function of particle radius, t(r), preferably is as follows:

$$t(r) = \left[\frac{3}{2} v\{G(r) - 1\} + 1\right]^{\frac{L}{2r}} \exp[-\mu_g L] \qquad (7)$$

with $$G(r) = 2\frac{e^{Cr}(Cr - 1) + 1}{(Cr)^2} \qquad (8)$$

and $$C = -2(\mu - \mu_g) = -2\Delta\mu. \qquad (9)$$

In this equation, r is the particle radius, v the volume percentage of the coarse grained component, L the length of the transmission path, $\mu$ the absorption coefficient of the coarse grained component and $\mu_g$ the absorption coefficient for the rest of the mixture (without the coarse grained component).

The relationship can be explained with reference, for the sake of simplicity, to a mixture consisting of a coarse grained component and a (homogeneous) remaining mixture. Then, integration provides the following for the average attenuation $\bar{t}$, of the gamma radiation over the particle cross section along a path 2r:

$$\bar{t} = G(r)\exp[-\mu_g 2r]. \qquad (10)$$

If the total volume of the heterogeneous mixture is now considered (transmission length L) as well as the mutual shading of the particles, equation (10) can be used to start a multiple integration and with the rules of combinatorial analysis in the form of equation (7) a particle size dependent relationship is obtained for the transmission, for the first time in a good approximation.

This relationship can be expanded to any desired mixtures by inserting the relevant parameters. For example, for the important case of a three-component mixture consisting of the components j=p, q, w, where p is coarse grained, and $\Delta\mu_j = \mu_j - \mu_w$ standardized for the third component, the following results from equation (7):

$$t(r) = \left[\frac{3}{2} v_p\{G(r) - 1\} + 1\right]^{\frac{L}{2r}} \exp\left[-L\frac{v_q}{1 - v_p}\Delta\mu_q\right] \qquad (11)$$

where G(r) is the same as in equation (8) and $$C = -2\left(\Delta\mu_p - \frac{v_q}{1 - v_p}\Delta\mu_q\right). \qquad (12)$$

In a similar way, relationships for multicomponent mixtures can be derived from equation (7). If there exists a plurality of coarse grained components, the first factor in equation (7) changes to a product wherein each factor contains the relevant parameters for a respective one of the coarse grained components. If a component is present which has particles that are not distinguished by a discrete radius r but by a size range, e.g. a Poisson distribution of the radii, this component should be divided in a suitable manner into a plurality of components having the same absorption coefficient but different discrete particle radii. Equation (7) thus represents the general basic equation for transmission analysis in the presence of coarse grained components.

Equation (7) or, for example, equation (11) are accessible only with difficulty to direct evaluation with respect to volume percentages or average density. Therefore, the particle size dependent- and energy dependent-transmission equation is advisably changed to the exponential form, analogously to the known transmission equations (1) or (2), respectively, i.e. in the case of the general equation (7)

$$t(r) = e^{-\mu_g L}e^{\frac{1}{2r}(\ln[\frac{3}{2} v\{G(r)-1\}+1])L}, \qquad (13)$$

one transforms, according to the invention, this equation to the simple exponential relationships analogous to equations (1) and (2) with the nomenclature used on page 11.

$$t^*(r) = e^{-\mu_g L}e^{-(V\Delta\mu)L} \qquad (14a)$$

or $$t(r) = e^{\mu_g L}e^{-(V\Delta\mu)^*L} \qquad (14b)$$

or $$t(r) = e^{-\mu_g L}e^{-v^*\Delta\mu L} \qquad (14c)$$

or $$t(r) = e^{-\mu_g L}e^{-v\Delta\mu^* L} \qquad (14d)$$

or $$t(r) = e^{-\mu_g L}e^{-v(\mu^* - \mu_g)L} \qquad (14e)$$

and determines, by comparison of coefficients, correction functions for the parameters marked with an asterisk. In other words, the influence of the finite particle size on the measuring result is shifted to these correction functions and the transmission measurement can be evaluated in a simple manner according to the invention, with the corrected values, even if coarse grained components are present.

From equations (13) and (14a) through (14e) follow the correction functions $$g(r) = \frac{t}{t^*(r)}$$

$$= \exp(-L)\left\{\frac{1}{2r}\ln\left[\frac{3}{2}v\{G(r)-1\}+1\right] + v\Delta\mu\right\}$$

(15a) (corresponding to 14a)

$$f(r) = \frac{(v\Delta\mu)^*}{v\Delta\mu} = \frac{v^*}{v} = \frac{\Delta\mu^*}{\Delta\mu}$$

$$= \frac{1}{vCr}\ln\left[\frac{3}{2}v\{G(r)-1\}+1\right]$$

(15b) (corresponding to 14b, 14c and 14d)

-continued as well as $$h(r) = \frac{\mu^*}{\mu} = \frac{1}{\mu}\left\{\mu_g - \frac{1}{2r\nu}\ln\left[\frac{3}{2}\nu\{G(r) - 1\} + 1\right]\right\} \quad \begin{array}{c}(15c)\\ \text{(corresponding}\\ \text{to 14e)}\end{array}$$

by division or comparison of the exponents, respectively.

Figure 3A:
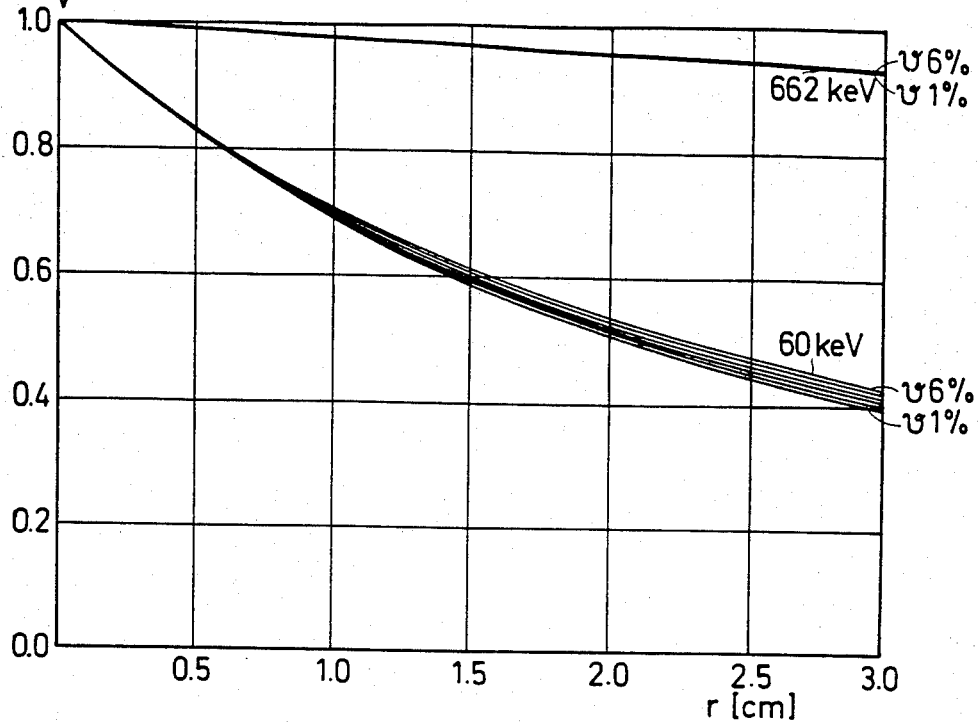
FIGS. 3a, 3b and 4 are diagrams illustrating the practice of the invention.
Figure 3B:
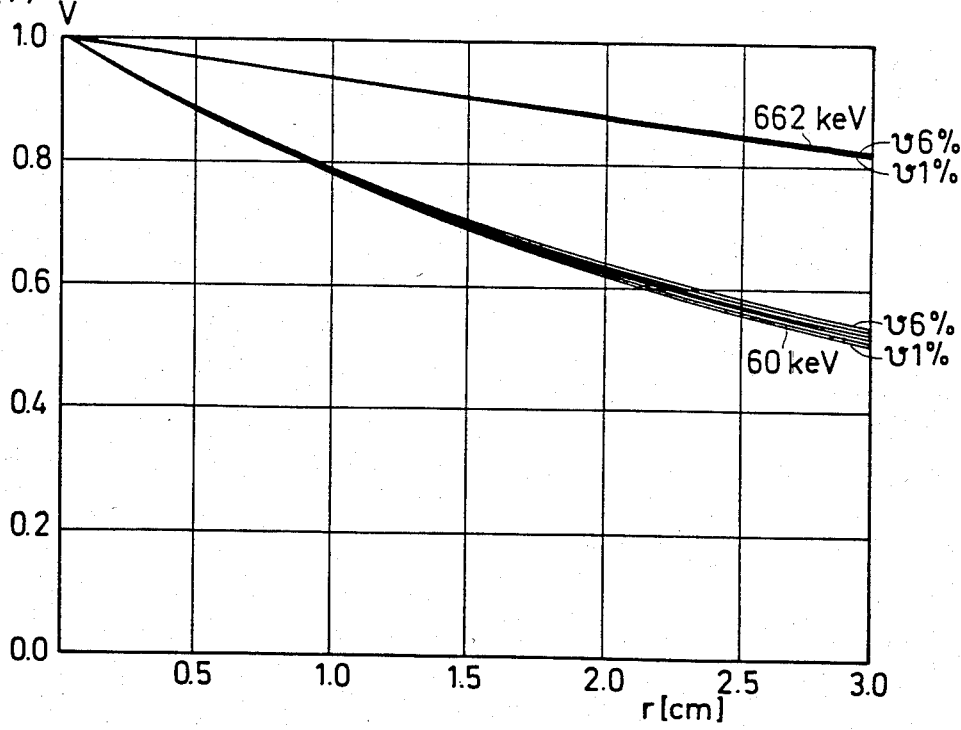

As can be seen, the correction functions are generally dependent on the volume percentage of the coarse grained component. The functions f(r) and h(r) have the advantage that this dependence is only very weak so that generally a function that has been calculated once from the absorption coefficients can be used for concentrations which vary over wide ranges. This is clarified by the relationships shown in FIGS. 3a and 3b with the example of function f(r) for two typical mixtures (Mn nodules and sea water in FIG. 3a, and steatite spheres and sea water in FIG. 3b), employing gamma radiation energies of 60 keV and 662 keV. Here, the parameter v represents the part by volume of the coarse-grained component. The curves shown represent the grain-radius dependency of the correction function or—in other words—the influence of grain size on the apparent part by volume.

To generalize these relationships for any desired mixtures the statements made above in connection with equation (7) apply correspondingly. In the case of a determination of the volume proportions in a three component mixture, f(r) will have the form $$f(r) = -\frac{1}{2r\nu_p \Delta\mu_p}\ln\left[\frac{3}{2}\nu_p\{F(r) - 1\} + 1\right] \quad (16)$$

with $$F(r) = 2\frac{1 - e^{-2r\Delta\mu_p}(1 + 2r\Delta\mu_p)}{(2r\Delta\mu_p)^2}. \quad (17)$$

Figure 4:
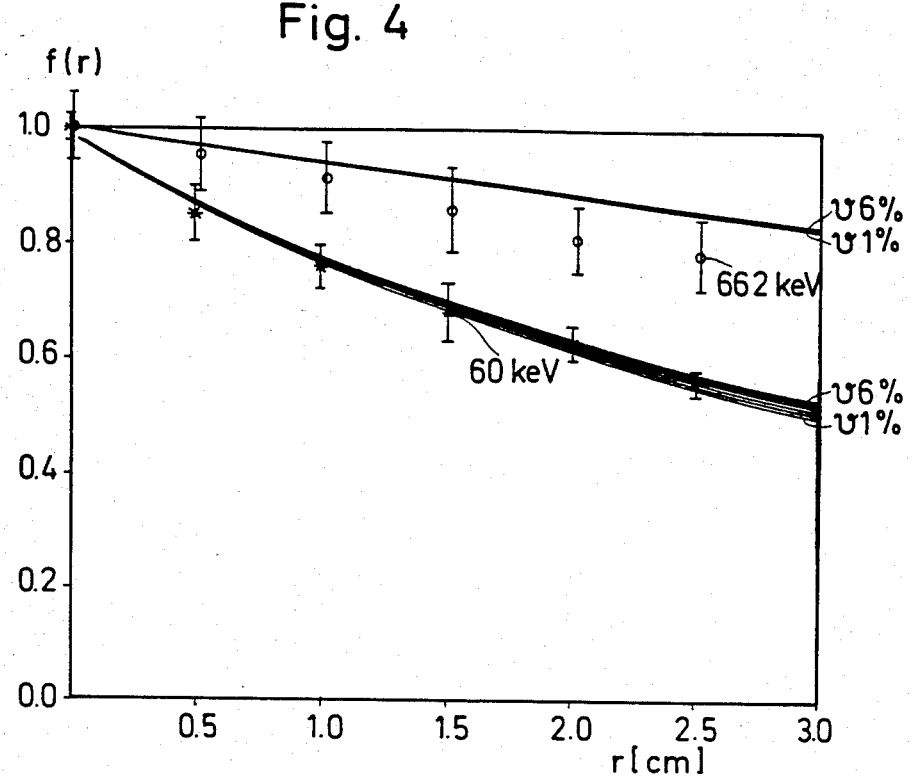

The method and an apparatus according to the present invention were tested with the aid of a hydraulic conveying circuit which permits flexible and controlled setting of the composition of the conveying stream. Steatite particles in the form of a granulate up to spheres of 5 cm diameter were used as the model substance. The material exhibited sufficient mechanical stability for these examinations and a gamma absorption coefficient which is similar to that of natural products. With a given composition, a correction function of the above type can be determined experimentally. The results derived from the invention were confirmed. FIG. 4 shows this for the example of the function f(r).

Figure 5:
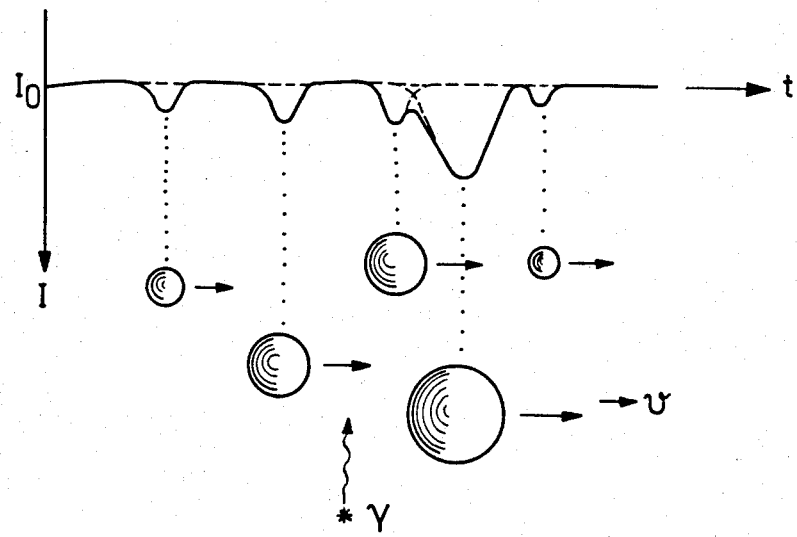
FIG. 5 is a partly pictorial diagram illustrating certain principles of the invention.
Figure 6:
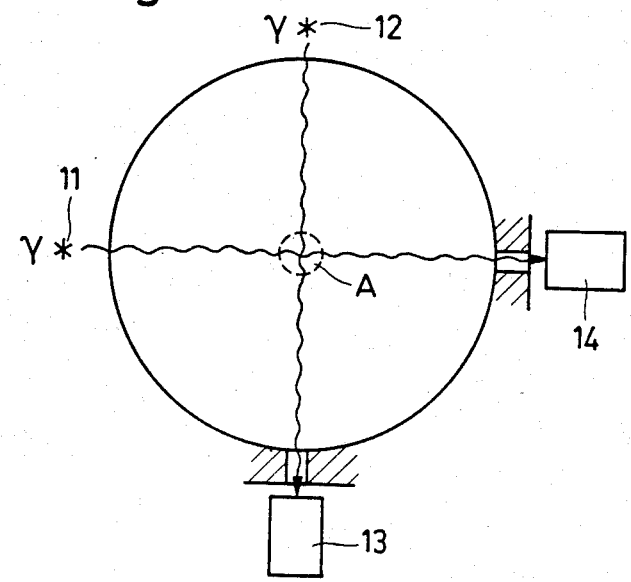
FIG. 6 is a view similar to those of FIGS. 2a-d relating to another embodiment of the invention.
Figure 7:
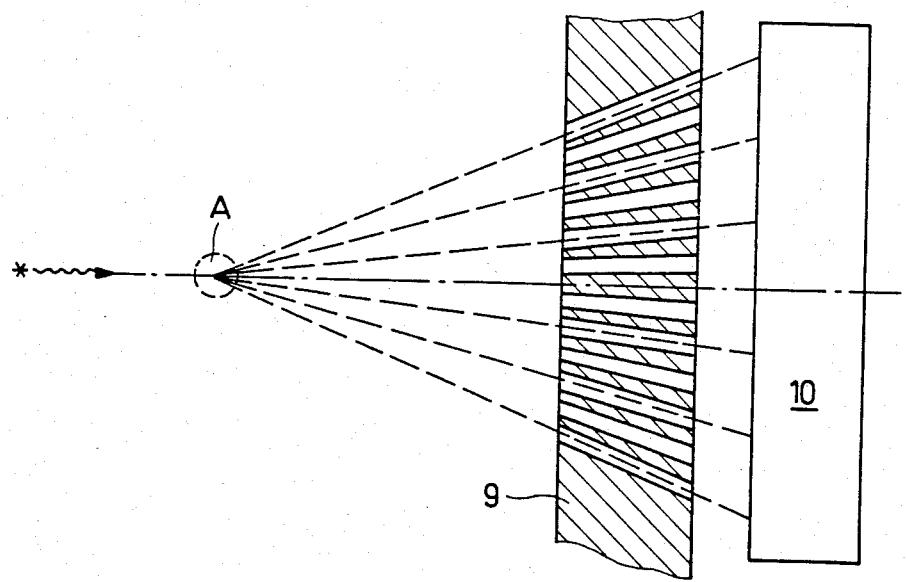
FIG. 7 is a pictorial, cross-sectional detail view of a component which can be employed in systems according to the invention.

If the particle radius is not known, it or its distribution can be measured with the same or a parallel device. If gamma radiation penetrates the mixture and a particle of a finite size passes through this "gamma barrier", the magnitude or duration, for example, of the momentary drop in the counting rate are a measure for the particle size. This is illustrated in FIG. 5, where the passage of each particle produces a drop in the radiation detector output which is proportional in amplitude and duration to the particle size. In the case of mutual shading, complex structures must be mathematically divided in a time dependent counting rate spectrum I(t), for example by means of a minicomputer. Other alternatives for the elimination of shading are to constrict the measuring volume A by cross-wise arrangement of two collimated gamma rays, as shown in FIG. 6 where two gamma sources 11 and 12 and two detectors 13 and 14 are arranged in two mutually perpendicular radiation paths which can be expanded by a corresponding arrangement of a plurality of "gamma barriers" in the same plane. Alternatively, as shown in FIG. 7, the constriction can be established by a conical multiple collimator 9 upstream of the detector 10, which is equivalent to fixing a locally defined scattering center A.

Commercially available data processors such as Zilog Z 80 (USA) can be employed to perform the calculations required to implement the invention.

Figure 8:
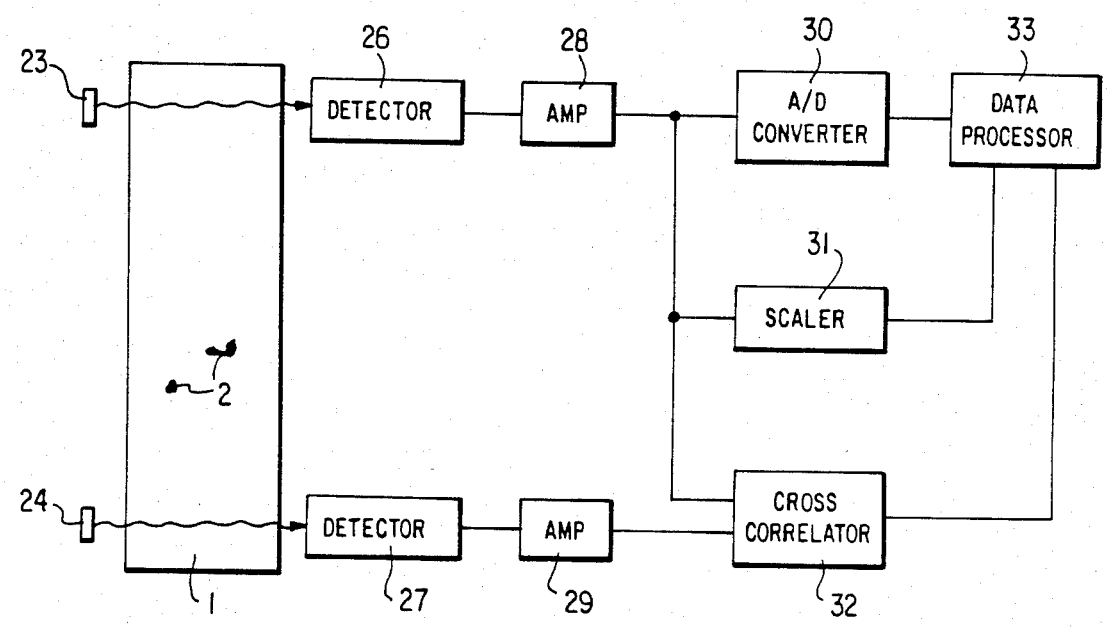
FIG. 8 gives a block diagram of an embodiment of a system with simultaneous determination of average density, parts by volume and particle-size distribution.

FIG. 8 shows a possible embodiment equivalent to one of the FIGS. 2a-d, in which the multicomponent mixture 1,2 is irradiated by two gamma beams from the sources 23, 24. The gamma rays are registered by the two detectors 26, 27. After amplification 28, 29 the counting rates are evaluated for determining the average density or parts by volume using an analog-to-digital converter 30 and simultaneously the particle size-distribution. The particle size is obtained by measuring the time sequence with the aid of a multichannel scaler 31 and the particle drift velocity by means of a cross correlater 32. Evaluation is achieved by means of the data processor 33.

It will be understood that the above description of the present invention is susceptible to various modifications, changes and adaptations, and the same are intended to be comprehended within the meaning and range of equivalents of the appended claims.

What is claimed is:

1. Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating a selected relation between the transmitted and detected radiation intensities to determine the average density or volume percentage by using a first transmission equation which defines the selected relation as a function of the average density or volume percentage in homogeneous mixtures, said step of evaluating comprising transforming the value of the selected relation resulting from solving the first equation with the aid of a correction function which is derived by comparison of corresponding values in the first transmission equation and in a further transmission equation which defines the selected relation as a function of the particle sizes of the coarse grained component in order to provide a corrected determination relative to that component.

2. Method as defined in claim 1 wherein the further transmission equation has the basic form, for a coarse grained component having a discrete particle radius (r), of $$t(r) = \left[\frac{3}{2}\nu\{G(r) - 1\} + 1\right]^{\frac{L}{2r}}\exp[-\mu_g L],$$

where $$G(r) = 2\frac{e^{Cr}(Cr-1)+1}{(Cr)^2};$$

$C = -2(\mu - \mu_g)$; v is the volume percentage of the coarse grained component; L is the length of the gamma radiation transmission path in the mixture; $\mu$ is the gamma radiation absorption coefficient of the coarse grained component; $\mu_g$ is the gamma radiation coefficient of the rest of the mixture; and t(r) is the transmission value, and can be expanded for any desired mixtures comprising a plurality of coarse grained components with discrete or arbitrarily distributed particle radii, and the correction function is:

$$g(r) = \exp(-L)\left\{\frac{1}{2r}\ln\left[\frac{3}{2}v\{G(r)-1\}+1\right] + v\Delta\mu\right\}.$$

3. Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating a selected relation between the transmitted and detected radiation intensities to determine the average density or volume percentage by using a first transmission equation which defines the selected relation as a function of the average density or volume percentage in homogeneous mixtures, said step of evaluating comprising transforming, in such equation, the term representative of the product of the volume percentage of the coarse grained component and the gamma radiation absorption coefficient of that component reduced by the gamma radiation absorption coefficient of the rest of the mixture, with the aid of a correction function which is derived by comparison of corresponding values in the first transmission equation and in a further transmission equation which defines the selected relation as a function of the particle sizes of the coarse grained component in order to provide a corrected determination relative to that component.

4. Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating a selected relation between the transmitted and detected radiation intensities to determine the average density or volume percentage by using a first transmission equation which defines the selected relation as a function of the average density or volume percentage in homogeneous mixtures, said step of evaluating comprising transforming, in such equation, the term representative of the volume percentage of the coarse grained component with the aid of a correction function which is derived by comparison of corresponding values in the first transmission equation and in a further transmission equation which defines the selected relation as a function of the particle sizes of the coarse grained component in order to provide a corrected determination relative to that component.

5. Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating a selected relation between the transmitted and detected radiation intensities to determine the average density or volume percentage by using a first transmission equation which defines the selected relation as a function of the average density or volume percentage in homogeneous mixtures, said step of evaluating comprising transforming, in such equation, the term representative of the gamma radiation absorption coefficient of the coarse grained component reduced by the gamma radiation absorption coefficient of the rest of the mixture, with the aid of a correction function which is derived by comparison of corresponding values in the first transmission equation and in a further transmission equation which defines the selected relation as a function of the particle sizes of the coarse grained component in order to provide a corrected determination relative to that component.

6. Method as defined in claim 3, 4 or 5 wherein the further transmission equation has the basic form, for a coarse grained component having a discrete particle radius (r) of $$t(r) = \left[\frac{3}{2}v\{G(r)-1\}+1\right]^{\frac{L}{2r}}\exp[-\mu_g L],$$

where $$G(r) = 2\frac{e^{Cr}(Cr-1)+1}{(Cr)^2};$$

$C = -2(\mu - \mu_g)$; v is the volume percentage of the coarse grained component; L is the length of the gamma radiation transmission path in the mixture; $\mu$ is the gamma radiation absorption coefficient of the coarse grained component; $\mu_g$ is the gamma radiation coefficient of the rest of the mixture; and t(r) is the transmission value, and can be expanded for any desired mixtures comprising a plurality of coarse grained components with discrete or arbitrarily distributed particle radii, and the correction function is:

$$f(r) = \frac{1}{vCr}\ln\left[\frac{3}{2}v\{G(r)-1\}+1\right].$$

7. Method for determining the average density or volume percentage of at least one coarse grained component of a multicomponent mixture by gamma transmission analysis, including the steps of irradiating the mixture with gamma radiation from at least one source, detecting the transmitted radiation by means of at least one detector, and evaluating a selected relation between the transmitted and detected radiation intensities to determine the average density or volume percentage by using a first transmission equation which defines the selected relation as a function of the average density or volume percentage in homogeneous mixtures, said step of evaluating comprising transforming, in such equation, the term representative of the gamma radiation absorption coefficient of the coarse grained component, with the aid of a correction function which is derived by comparison of corresponding values in the first transmission equation and in a further transmission equation which defines the selected relation as a function of the particle sizes of the coarse grained component in order to provide a corrected determination relative to that component.

8. Method as defined in claim 1, 3, 4, 5 or 7 wherein the further transmission equation has the basic form, for a coarse grained component having a discrete particle radius (r), of $$t(r) = \left[ \frac{3}{2} v\{G(r) - 1\} + 1 \right]^{\frac{L}{2r}} \exp[-\mu_g L],$$

where $$G(r) = 2 \frac{e^{Cr}(Cr - 1) + 1}{(Cr)^2};$$

$C = -2(\mu - \mu_g)$; v is the volume percentage of the coarse grained component; L is the length of the gamma radiation transmission path in the mixture; $\mu$ is the gamma radiation absorption coefficient of the coarse grained component; $\mu_g$ is the gamma radiation coefficient of the rest of the mixture; and t(r) is the transmission value, and can be expanded for any desired mixtures comprising a plurality of coarse grained components with discrete or arbitrarily distributed particle radii.

9. Method as defined in claim 7 wherein the further transmission equation has the basic form, for a coarse grained component having a discrete particle radius (r), of $$t(r) = \left[ \frac{3}{2} v\{G(r) - 1\} + 1 \right]^{\frac{L}{2r}} \exp[-\mu_g L],$$

where $$G(r) = 2 \frac{e^{Cr}(Cr - 1) + 1}{(Cr)^2};$$

$C = -2(\mu - \mu_g)$; v is the volume percentage of the coarse grained component; L is the length of the gamma radiation transmission path in the mixture; $\mu$ is the gamma radiation absorption coefficient of the coarse grained component; $\mu_g$ is the gamma radiation coefficient of the rest of the mixture; and t(r) is the transmission value, and can be expanded for any desired mixtures comprising a plurality of coarse grained components with discrete or arbitrarily distributed particle radii, and the correction function is:

$$h(r) = \frac{1}{\mu} \left( \mu_g - \frac{1}{2rv} \ln \left[ \frac{3}{2} v\{G(r) - 1\} + 1 \right] \right).$$

10. Apparatus for determining the average density or volume percentage of at least one coarse grained component of a multicomponent mixture by gamma transmission analysis, comprising: means including at least one gamma radiation source for irradiating the mixture with gamma radiation; means including at least one gamma radiation detector for detecting the transmitted radiation; and means connected to said detector for evaluating a selected relation between the transmitted and detected radiation intensities to determine the average density or volume percentage by using a first transmission equation which defines the selected relation as a function of the average density or volume percentage in homogeneous mixtures, said means for evaluating being operative to transform the values resulting from solving the first equation, or a selected term thereof, with the aid of a correction function which is derived by comparison of corresponding values in the first transmission equation and in a further transmission equation which defines the selected relation as a function of the particle sizes of the coarse grained component in order to provide a corrected determination relative to that component.

11. Apparatus as defined in claim 10 wherein there is a plurality of said sources and a plurality of said detectors each associated with a respective source and defining a beam path with its associated source.

12. Apparatus as defined in claim 11 wherein all of the beam paths are coaxial.

13. Apparatus as defined in claim 11 wherein the beam paths are offset from one another.

14. Apparatus as defined in claim 13 wherein the beam paths are in a common plane and intersect to create a constricted region within the mixture which is common to all beam paths.

15. Apparatus as defined in claim 10 further comprising a conical multiple collimator disposed in the path of the radiation between said source and said detector for causing radiation to reach said detector from a constricted region within the mixture.

16. Apparatus as defined in claim 10 further comprising means connected to said detector for analyzing the time sequence of the counting rate produced by said detector in order to determine the particle radii of the coarse grained component.

17. Apparatus as defined in claim 16 wherein said means for analyzing operate to evaluate the magnitude or duration of each drop in the counting rate produced by said detector.

* * * * *